United States Patent
Hulme et al.

(10) Patent No.: US 8,687,184 B2
(45) Date of Patent: Apr. 1, 2014

(54) REFERENCE CELL

(75) Inventors: Keith Hulme, Essex (GB); John Hammond, Essex (GB)

(73) Assignee: Starna Scientific Limited (GB)

( * ) Notice: Subject to any disclaimer, the term of this patent is extended or adjusted under 35 U.S.C. 154(b) by 318 days.

(21) Appl. No.: 12/866,272

(22) PCT Filed: Feb. 12, 2009

(86) PCT No.: PCT/GB2009/000405
§ 371 (c)(1),
(2), (4) Date: Oct. 4, 2010

(87) PCT Pub. No.: WO2009/101418
PCT Pub. Date: Aug. 20, 2009

(65) Prior Publication Data
US 2011/0013182 A1    Jan. 20, 2011

(30) Foreign Application Priority Data

Feb. 12, 2008  (GB) .................................. 0802574.4

(51) Int. Cl.
| | |
|---|---|
| *G01N 21/01* | (2006.01) |
| *G01N 1/10* | (2006.01) |
| *G01N 21/41* | (2006.01) |
| *G01N 21/00* | (2006.01) |
| *G01J 3/28* | (2006.01) |
| *G01J 5/02* | (2006.01) |
| *G01N 21/49* | (2006.01) |
| *H01J 5/02* | (2006.01) |

(52) U.S. Cl.
USPC ........... 356/244; 356/436; 356/133; 356/440; 356/458; 356/246; 356/326; 250/339; 250/576; 250/239

(58) Field of Classification Search
USPC ......... 356/436, 133, 440, 458, 244, 246, 326; 250/339, 576, 239
See application file for complete search history.

(56) References Cited

U.S. PATENT DOCUMENTS

| | | | | |
|---|---|---|---|---|
| 4,375,164 | A | * | 3/1983 | Dodge et al. ................ 73/152.12 |
| 5,173,749 | A | * | 12/1992 | Tell et al. ....................... 356/437 |
| 5,572,031 | A | * | 11/1996 | Cooper et al. ................. 250/343 |
| 6,064,488 | A | * | 5/2000 | Brand et al. ................... 356/440 |
| 6,886,406 | B1 | * | 5/2005 | Couet et al. ...................... 73/579 |
| 2004/0086215 | A1 | * | 5/2004 | Salerno et al. .................. 385/12 |
| 2008/0040062 | A1 | * | 2/2008 | Kalar et al. ...................... 702/99 |

OTHER PUBLICATIONS

Toptica Photonics, Herriott Type Cell Multipass Cell, Jan. 2004, Toptica Photonics AG.*

* cited by examiner

*Primary Examiner* — Tarifur Chowdhury
*Assistant Examiner* — Sunghee Y Gray
(74) *Attorney, Agent, or Firm* — Stites & Harbison, PLLC; David W. Nagle, Jr.; Stephen J. Weyer

(57) ABSTRACT

Reference cell (8) for use with a fiber optic probe (1) comprising a base wall (11), upstanding walls (12) each having an optical window (13, 15), and a top wall (14) having a further optical window (16) adapted to allow light to pass to and from a fiber optic probe. The base wall (11) comprises a reflector (19) which reflects incident light from the fiber optic probe back to said probe (1). The top wall (14) has an attachment for receiving an emitting and a receiving end of a fiber optic probe (1). The cell (8) allows use of standard fiber optic probe (1) with other optical equipment when the path length and the probe optical characteristics require validation to international standards. The calibration of the probe (1) is analogous to calibration of laboratory spectrophotometers and can therefore be validated. The device (8) enables probes (1) to be used for applications where precision and accuracy are essential.

6 Claims, 2 Drawing Sheets

REFERENCE CELL

The invention relates to a reference cell, in particular for use in conjunction with fibre optic probes.

Fibre optic probes have long been used to measure the properties of solutions. Such probes use optical fibres to transmit light to interact with the solution. The transmitted light is then picked up by the optical fibres and the characteristics of this received light will have been modified by the interaction with the solution. Analysis of this received light provides information on the characteristics of the solution. Fibre optic probes can be used in a wide range of applications.

An example of such a fibre optic probe is disclosed in U.S. Pat. No. 6,879,741, which probe comprises a handle, optical fibres extending from the handle and a sampling end positionable over the optical fibres. The sampling end comprises a releasably attached tube member having an open end and a closed end. The fibre optics extend from the handle into the sampling end through the open end of the tube member. The closed end of the tube member is provided with an optical window to enable light to pass to and from the optical fibres. In use, a tip is attached to the optical window. The tip comprises a further tubular member of substantially rectangular cross-section, which is open at two opposed sides perpendicular to the open and closed ends of the tube member. The wall of the further tubular member adjacent to the aforementioned optical window also comprises an optical window, whereas the opposed wall of the further tubular member comprises a reflector. In use, the tip end is inserted into a solution and the light emitted by the optical fibre is reflected by the reflector back towards the optical fibres after passing through the solution, thereby enabling the characteristics of the solution to be detected. The probe is calibrated by the knowledge of the user of the wavelength of light emitted by the optical fibres and the path length between the optical window and the reflector of the tip.

This type of fibre optic probe has established itself in the market place, in particular for use with corrosive or difficult to clean samples such as with biotech and medical analysis or petrochemical solutions, where it is quick and efficient. The probe does, however, suffer from the problem of limited accuracy and precision for certain applications as it is not possible to calibrate the probe in accordance with the mandated standards in the medical and pharmaceutical fields and so results cannot be validated.

The present invention therefore seeks to provide an accurate method to validate such a fibre optic probe that can be used to make validated measurements.

According to the invention, there is provided a reference cell for use with a fibre optic probe characterised in that said cell comprises a base wall, first and second opposed upstanding walls and further walls each having an optical window, which further walls are perpendicular to the said opposed upstanding walls and a top wall, which top wall is provided with a further optical window, which further optical window is adapted to permit transmission of light to and from a fibre optic probe, which walls define a chamber, wherein the chamber is provided with a reference material.

Preferably, the further walls are optical windows. Preferably the base wall comprises a reflector adapted to reflect incident light from a fibre optic probe back to the fibre optic probe. Preferably, the top wall comprises an attachment adapted to receive an emitting and receiving end of a fibre optic probe. Preferably, a sealable opening is provided to enable the reference material to be placed into the cell.

The method advantageously permits the use of standard fibre optic probes in conjunction with other optical equipment such as spectrophotometers, in situations where it is necessary that the path length, defined as the internal distance between opposite windows, together with the optical characteristics of the probe need to be validated.

An exemplary embodiment of the invention will now be described in greater detail with reference to the drawings, in which.

Figure 1:
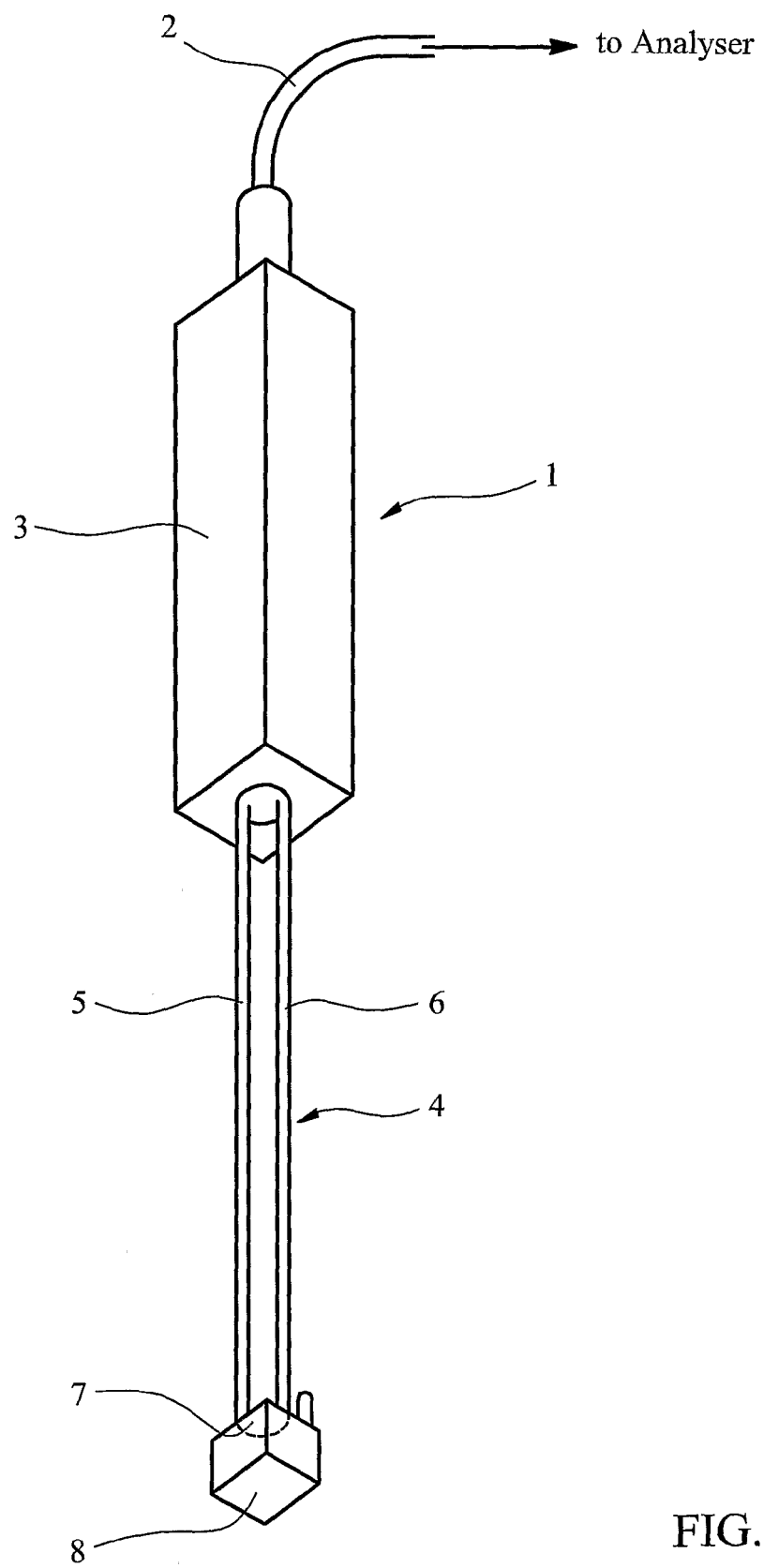
FIG. 1 shows a fibre optic probe.

FIG. 1 shows schematically a fibre optic probe device 1. The device comprises a fibre optic cable 2 having a first input optical fibre and a second output optical fibre, which cable 2 is fed into one end of the probe handle 3. The cable 2 is connected at the end remote from the handle to an analyzer adapted to process the output of the output optical fibre. The input and output optical fibres extend through the handle 3 to a sampling end cylindrical tube 4. The input optical fibre 5 and output optical fibre 6 are visible in the sampling end tube 4 and extend to its distal end, which is provided with an optical window 7, which closes the distal end of the tube 4. The tube and fibres are shown schematically as dimensions and shape may vary depending on the precise intended application of the device 1. A reference tip 8 is provided at the end of the tube 7 that comprises a sample chamber suitable for containing a reference material suitable for calibrating a spectrophotometer. Exemplary reference materials include potassium dichromate and holmium oxide.

Figure 2:
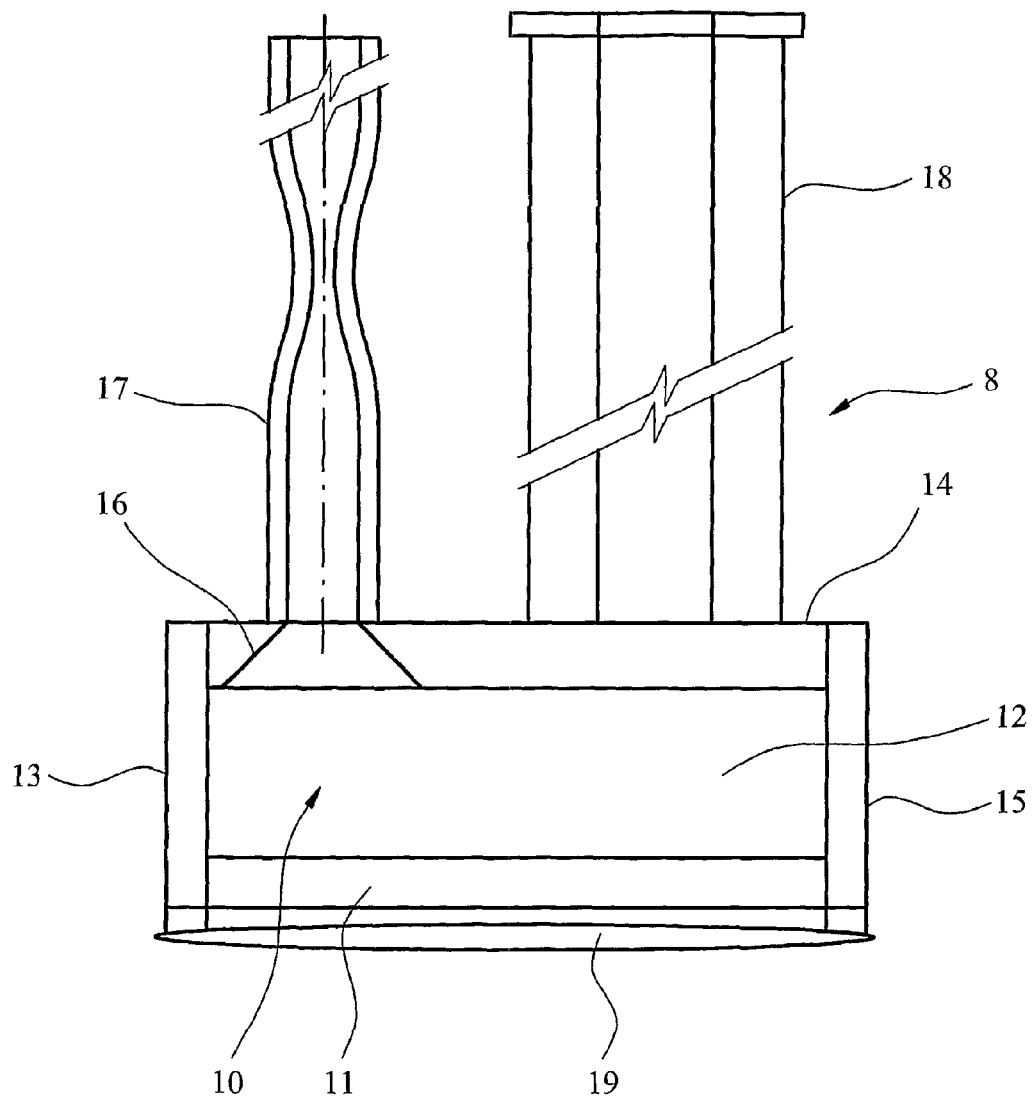
FIG. 2 shows a reference tip for the probe of FIG. 1

FIG. 2 shows the reference tip 8 in greater detail. The tip 8 comprises a sample chamber 10 having a base 11, first and second upstanding walls 12 and a top wall 14. The chamber is provided with first and second optical windows 13, 15 so that light from a spectrophotometer can, in use, pass transversely through the sample chamber 10. The optical windows 13, 15 can be manufactured from quartz materials such as Spectrosil™. The top wall 14 is provided with an opening 16 which leads to a restricted tubular opening 17. Prior to use, the sample chamber 10 will be filled with a reference material such as potassium dichromate via the crimped tubular opening 17, which can then be sealed using known techniques. The sealed tube also acts as an expansion chamber for the liquid contained in the cell and a trap for the air bubble to reside out of the main chamber of the cell Adjacent to the opening 16, a connector 18 is provided, which connector is adapted to connect to or slide over the distal end of the tube 4. An optical window is provided at the base of the connector 18, so that light from the probe fibre 5 can enter the sample chamber 10 and be reflected back by a reflective coating 19 provided on the base 11. The base 11 is also slightly inclined on its lower surface so that it is not parallel to the upper surface of the base so as to enable the incident light to be reflected back precisely to the optical fibre receiver.

The reference tip 8 can be used in both a spectrophotometer and by a conventional fibre optic probe. Therefore, it is possible to create a reference cell for the fibre optic probe as the ability to use the tip in a spectrophotometer permits the manufacturer to validate the cell to the international standards required by standards bodies such as European Pharmacoepia. The calibration of a fibre-optic probe can then be validated in the laboratory in the analogous fashion to laboratory spectrophotometers and can thus be used in a wide range of medical applications where high levels of precision and accuracy are required.

The invention claimed is:

1. A method for validating path length and optical characteristic of a fibre optic probe, the method comprising the steps of:
(a) providing a fibre optic probe reference cell (8) comprising a base wall (11), first and second opposed upstanding walls (12) and further walls, which further walls are perpendicular to the opposed upstanding walls, each further wall having an optical window (13, 15), the cell further comprising a top wall (14), which top wall (14) is provided with a further optical window (16), which further optical window (16) is adapted to permit transmission of light to and from a fibre optic probe (1), which walls (11, 12, 14) define a chamber (10), wherein the chamber (10) is provided with a reference material and wherein the base wall (11) comprises a reflector (19) adapted to reflect incident light from a fibre optic probe (1) back to said fibre optic probe (1);
(b) connecting the fibre optic probe reference cell (8) to the fibre optic probe (1) comprising a fibre optic cable (2) having a first input optical fibre (5) and a second output optical fibre (6), which first input and second output optical fibres (5, 6) extend to a sampling end (4), said fibre optic cable (2) being connected at an end to an analyzer adapted to process the first input optical fibre (5) and the second output optical fibre (6);
(c) transmitting light through the first input optical fibre (5) into the chamber (10) to interact with the reference material;
(d) transmitting incident light back to the fibre optic probe (1) to determine path length of the fibre optic probe reference cell (8) and absorption characteristics of the reference material;
(e) calibrating the fibre optic probe (1) based on the path length of the fibre optic probe reference cell (8) and the absorption characteristics of the reference material; and
(f) validating the calibration step by determining the path length of the fibre optic probe reference cell (8) and the absorption characteristics of the reference material in a spectrophotometer.

2. The method for validating path length and optical characteristic of a fibre optic probe according to claim 1, wherein the step of connecting the fibre optic probe reference cell (8) to a fibre optic probe (1) is performed by providing an attachment (18) on the top wall (14), which attachment (18) is adapted to receive an emitting and receiving end of a fibre optic probe (1).

3. The method for validating path length and optical characteristic of a fibre optic probe according to claim 1, the method further comprising the step of providing a sealable opening (16) to enable the reference material to be placed into the cell.

4. The method for validating path length and optical characteristic of a fibre optic probe according to claim 1, wherein the further walls are optical windows.

5. The method for validating path length and optical characteristic of a fibre optic probe according to claim 2, the method further comprising the step of providing a sealable opening (16) to enable the reference material to be placed into the cell.

6. The method for validating path length and optical characteristic of a fibre optic probe according to claim 2, wherein the further walls are optical windows.

* * * * *